United States Patent [19]

Hauber

[11] Patent Number: 5,201,762
[45] Date of Patent: Apr. 13, 1993

[54] INTRAOCULAR ARCHROMATIC LENS

[76] Inventor: Frederick A. Hauber, 13910 Fivay Rd., Hudson, Fla. 33567

[21] Appl. No.: 767,556

[22] Filed: Sep. 27, 1991

Related U.S. Application Data

[63] Continuation of Ser. No. 496,159, Mar. 19, 1990, abandoned, which is a continuation of Ser. No. 340,288, Apr. 19, 1989, abandoned, which is a continuation-in-part of Ser. No. 51,825, May 20, 1987, abandoned.

[51] Int. Cl.$^5$ .......................... A61F 2/16; A61F 2/14
[52] U.S. Cl. ............................................ 623/6; 623/5
[58] Field of Search ................... 351/160 R; 623/5, 6

[56] References Cited

U.S. PATENT DOCUMENTS

| | | | |
|---|---|---|---|
| 3,976,364 | 8/1976 | Lindemann | 351/43 |
| 4,074,368 | 2/1978 | Louy | 623/6 |
| 4,097,141 | 6/1978 | Warner | 350/503 |
| 4,429,956 | 2/1984 | Herbert | 351/160 R |
| 4,504,982 | 3/1985 | Burk | 623/6 |
| 4,641,934 | 2/1987 | Freeman | 351/160 R |
| 4,642,112 | 2/1987 | Freeman | 623/6 |
| 4,655,565 | 4/1987 | Freeman | 351/159 |
| 4,710,197 | 12/1987 | Donn | 351/160 R |
| 4,731,078 | 3/1988 | Stoy et al. | 623/6 |
| 4,981,342 | 1/1991 | Fiala | 350/403 |
| 5,017,000 | 5/1991 | Cohen | 351/161 |

FOREIGN PATENT DOCUMENTS 8603961 7/1986 World Int. Prop. O. .............. 623/6

OTHER PUBLICATIONS

Veldkamp et al., "Binary Optics", Scientific American, May 1992, pp. 92-97.
Hecht et al., Optics, Addison-Wesley: Reading, Mass., 1974, pp. 375-376.
Hecht et al., Optics, Addison-Wesley: Reading, Mass., 1974, p. 42.
Hecht et al., Optics, Addison-Wesley: Reading, Mass., 1974, pp. 187-188.
"Problems and Compromises in the Design of Aspheric Cataract Lenses", Davis, American Journal of Optometry and Archives of American Academy of Optometry, Jun. 1959, vol. 36 #6 p. 279.

Primary Examiner—David Isabella
Assistant Examiner—David Willse
Attorney, Agent, or Firm—James Creighton Wray

[57] ABSTRACT

An intraocular achromatic lens system has an intraocular achromatic lens positioned within the posterior and anterior chambers of the eye and in optical alignment with one or more intraocular lenses. The intraocular lenses operate in conjunction with each other to act as an internal multiple lens system for projecting an image upon the retina, which may be used to provide magnification. The intraocular lens includes a lens positioned in direct alignment and in close proximity with the pupil in the anterior chamber of the eye. The intraocular lens system also includes a lens positioned within the posterior chamber of the eye with a lens body having a sign opposite to the first lens body. The intraocular lens system may also include single or multiple lenses within the vitreal chamber of the eye and/or an intracorneal lamellar inlay or achromatic lenses.

27 Claims, 1 Drawing Sheet

INTRAOCULAR ARCHROMATIC LENS

This is a continuation of U.S. application Ser. No. 07/496,159, filed Mar. 19, 1990, now abandoned, which is a continuation of U.S. application Ser. No. 07/340,288, filed Apr. 19, 1989, now abandoned, which is a continuation-in-part of U.S. application Ser. No. 07/051,825, filed May 20, 1987, now abandoned.

BACKGROUND OF THE INVENTION

Intraocular lenses of the type described herein are used primarily to treat problems of vision in a human eye.

The image which would normally be directed to a damaged or diseased area of a retina is refocussed to another area of a retina so that vision may be improved.

A normal eye has two lenses with four refracting surfaces. Both lenses are convergent lenses which tend to focus light rays inward toward an axis of the eye. Greatest refraction takes place at the air-cornea interface and lesser refraction occurs at the cornea-aqueous humour interface. Refraction again occurs at the aqueous humour-crystalline lens interface and again at the crystalline lens-vitreous humour interface. The aqueous humour and vitreous humour have approximately the same refractive index which is slightly below the refractive indices of the cornea and crystalline lens. The crystalline lens is composed of the capsule, the cortex and the nucleus, all of these surfaces having different indices of refraction allowing for color correction of incoming wavelengths of light.

When a crystalline lens is removed because of occlusion, for example, with cataracts, its function may be replaced by a relatively thick converging lens worn outside of the eye. Preferably in removing the crystalline lens the capsule is held intact to maintain separation between the vitreous humour and the aqueous humour.

In recent times an intraocular lens is surgically positioned in the posterior chamber of the eye behind the iris and in front of the capsule. The introacular lens, called a pseudophakos, is held in place with a haptic which extends outward from the lens and engages the outer wall of the posterior chamber or the sulcus. In another mounting method the lens may be attached directly to the iris or the chamber angle or within the cornea by any known means.

The pseudophakos has the advantage of eliminating the requirement for thick eyeglasses and increasing the field of vision as compared with thick eyeglasses which may be used to replace a removed crystalline lens.

Techniques are known for anchoring a lens within the eye.

When a normal eye gazes upon a distant object the cornea and crystalline lens focus an object upon a part of the retina which is in optical alignment with those lenses and which is called the macula which joins the retina with the optic nerve and which is most sensitive to light.

A common problem which may develop especially in elderly persons, is loss of color correction on the surface of the retina due to the inability of current lenses to correct the color wavelengths of light adequately. The achromatic lens will improve the color correction problem and thus improve overall image quality.

Current intraocular lenses are made of glass, plastics, silicone or hydrogel.

The use of a single element lens will allow for a focus of some wavelengths of light, but will cause a blur for other wavelengths.

The construction of achromatic lenses is a well-known process. Fine controlled forming, molding and grinding, matching spherical and nonspherical concave and convex or planar surfaces on lenses and joining exact opposite surfaces together with bonding material is known in the art.

Glass, such as combined lenses of flint and crown glass chosen for their different refractive indices may be joined together as an achromatic lens or plastics having different indices of refraction may be joined together or may be combined with glass of the desired index of refraction. One plastic well known for use in intraocular lenses is methyl methacrylate. Other suitable materials are known such as polycarbonate silicone, hydrogel, or glass. One basic plastic may be used and impregnated with materials which provide differing indices of refraction in separate lens elements of the achromatic lens. The use of an achromatic lens consisting of two materials of different refractive indices will allow for better color correction than lenses currently described.

RELATION TO THE PARENT APPLICATION

This invention is described in the parent application, particularly with reference to FIGS. 13 and 15, and in the specification wherein it is stated that an achromatic intraocular lens for use in the system is made of two optical lens components cemented together to form a doublet. The two lenses are preferably made of materials having different refractive indices so that refraction occurs at the interface as well as at the distal and proximal surface of the joined multiple lenses. Provided the appropriate degree of magnification or relocation of the image on the retina may be accomplished by the achromatic lens, that lens is the preferred multiple intraocular lens system.

The present invention describes the use and positioning of achromatic lenses within the posterior and anterior chamber of the eye and describes the use of different forms of achromatic lenses to treat different requirements.

SUMMARY OF THE INVENTION

The present invention provides intraocular achromatic lenses. In a preferred embodiment the achromatic lens is positioned in a posterior chamber of an eye. In another preferred form of the invention the achromatic lens may be positioned in an anterior chamber of the eye.

The achromatic lens is made of two portions having different refractive indices. Preferably both portions are convergent. One portion may be convergent and the other portion may be divergent or both portions may be divergent.

A divergent achromatic lens may be used, for example, when a normal functional crystalline lens is present or when a pseudophakos has replaced an occluded crystalline lens and wherein it is difficult or unnecessary to remove the pseudophakos or normal crystalline lens.

The purpose of the achromatic lens of the present invention is the usual improved image quality or improved color correction which also enhances the image quality over current areas.

Further and other objects and features of the invention are apparent in the disclosure which includes the

DETAILED DESCRIPTION OF THE DRAWINGS

Figure 1:
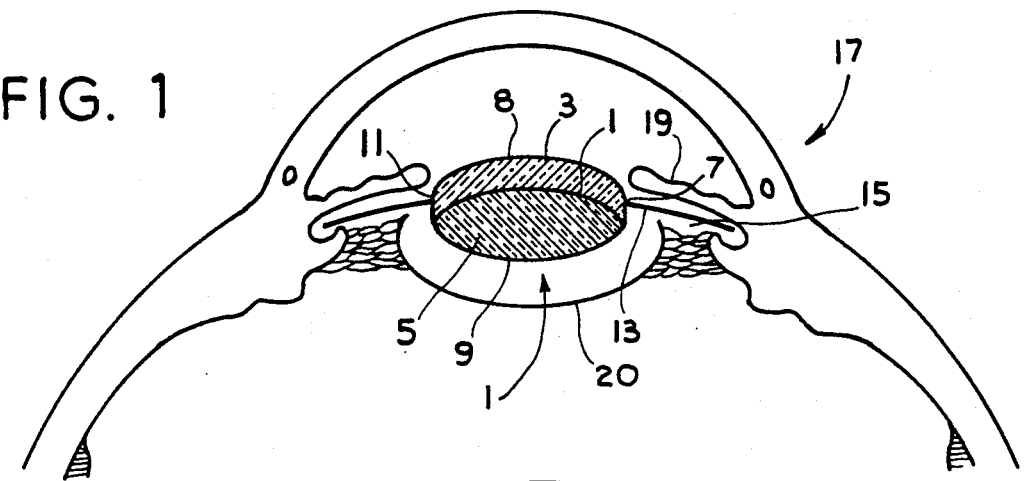
FIG. 1 is a schematic view of a frontal portion of an eye from which a crystalline lens has been removed and in which an achromatic lens has been placed in the posterior chamber.

FIG. 1 shows an achromatic lens 1 having a front lens portion 3 and a rear lens portion 5 joined together along a commonly shaped interface 7. Refraction occurs at the aqueous humour front lens interface 8, at the lens interface 7 and at the aqueous humour rear lens interface 9. In the embodiment shown in FIG. 1 both lenses are convergent lenses, lens 3 being slightly thicker at its center than at its outer edge 11 and the curvature of surface 3 being slightly greater than the curvature of interface 7.

A conventional haptic 13 extends outward to engage an outer surface of the posterior chamber 15 between the sulcus 16 and the iris 19.

Eye 17 has a cornea 18. The greatest refraction in the eye occurs at the cornea-air interface.

Capsule 20 is shown with a crystalline lens removed.

Figure 2:
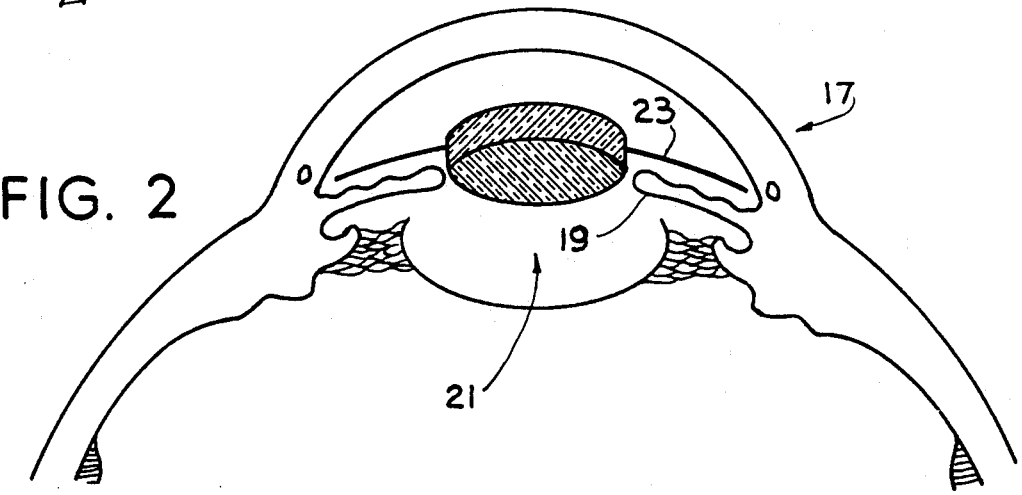
FIG. 2 is a similar view of an eye in which an achromatic lens has been replaced in an anterior chamber.

As shown in FIG. 2, achromatic lens 21 is positioned in the anterior chamber 22 of eye 17. Haptic 23 extends from the side of the achromatic lens to an outer wall of the anterior chamber just in front of the iris 19.

Achromatic lens 21 has a similar configuration to the achromatic lens 1 shown in FIG. 2.

Figure 3:
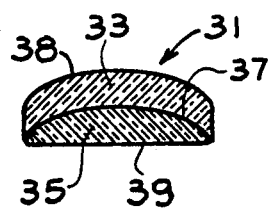
FIGS. 3, 4, 5 and 6 are details of differing forms of achromatic lenses.

In FIG. 3 an achromatic lens 31 is formed of two convergent lenses 33 and 35 having a common interface 3. Refraction occurs at the outer surface 38, the interface 37 and the planar rear face 39.

Figure 4:
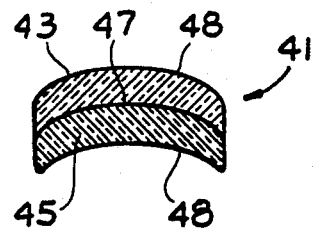

FIG. 4 shows an intraocular achromatic lens 41 in which both lenses 43 and 45 are convergent lenses and in which both lenses 43 and 45 are convex-concave lenses. In lens 41 the curvature of surface 48 is greater than the curvature of interface 47 and the curvature of surface 49 is less than the curvature of interface 47. A haptic may be mounted anywhere on the outer surface of the lens and may be mounted at the outer edge of the interface 47.

Figure 5:
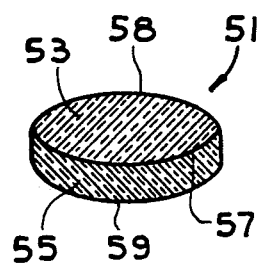

The intraocular achromatic lens 51 shown in FIG. 5 is similar to lens 1 shown in FIG. 1, with the exception that the convex-convex portion 53 is located in the front of the lens and the concave-convex portion 55 is located at the rear of the lens. Refraction occurs at the outer surfaces 58 and 59 and at the interface 57. The lenses 53 and 55 are of different indices of refraction.

Figure 6:
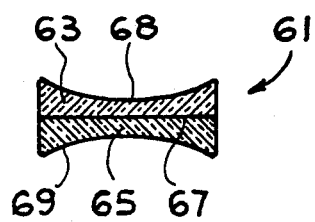

As shown in FIG. 6, a divergent intraocular achromatic lens has two divergent lens portions 63 and 65 joined at a planar interface 67. Refraction occurs at the concave surfaces 68 and 69 and at the interface 67. Lens 61 shown in FIG. 6 may be used in conjunction with an existing crystalline lens or pseudophakos. The haptic may be connected to one of the two lens portions 63 or 65 or may be connected at the outer edge of the interface 67.

One form of an achromatic lens is comprised of an intracorneal lamellal implant; one can be used in aqueous iris fixation, or one fixated within the vitreous. The intraocular achromatic lens may be used in combination with other lenses, either internal or external or placed in an orientation to produce prismatic effects.

While the lenses are shown for purposes of illustration in relatively thick embodiments, in the preferred form of the invention the peripheral areas of the lenses are reduced to as small as practical an axial dimension. The refracting surfaces of the lenses are emphasized for purposes of illustration and the actual refracting surfaces may be quite different depending on the requirements of individual eyes. Preferably, the refraction is arranged in the example of macular degeneration so that the image projected upon the retina is enlarged so that it covers the retina in areas around the macula.

For purposes of illustration, the lenses are shown with a substantial axial dimension. In practice, the axial dimension of the lenses may be reduced. The actual desired position of the lens is spaced inward or outward from the iris in the posterior chamber or capsule or in the anterior chamber. The preferred axial displacement of the intraocular achromatic lens from the iris allows the normal contraction and expansion which occurs with light variations to control pupillary size.

In some cases a capsule may have been destroyed with attendant failure of separation between the vitreous and aqueous fluid. In that case, the achromatic lens and the haptic may be designed to support the lens in a rearward position within the eye. Under that circumstance, it is preferable to mount the haptic in the posterior chamber or to otherwise connect the haptic to the sulcus.

While the invention has been described with reference to specific embodiments, modifications or variations of the invention may be constructed without departing from the scope of the invention. The scope of the invention is defined in the following claims.

I claim:

1. An intraocular achromatic lens system comprising two intraocular lenses having distinct refractive indices and distinct optical powers for surgically positioning in optical alignment within an eye, the plural lenses being joined together as an achromatic lens and means connected to the achromatic lens for mounting the lens totally within a posterior or anterior chamber of an eye.

2. The lens system of claim 1 wherein the achromatic lens is adapted to be mounted within the posterior chamber of the eye.

3. An intraocular achromatic lens comprising a first lens having a first refractive index and a second lens having a second refractive index, the first lens and the second lens being joined together at an interface to form an achromatic lens, the achromatic lens having a size suitable for positioning in an anterior chamber or a posterior chamber of an eye and the achromatic lens having a peripheral mounting element for mounting the achromatic lens within one of the posterior or anterior chambers of the eye.

4. The apparatus of claim 3 wherein the mounting means comprises a haptic connected to a peripheral portion of one of the lenses which make up the achromatic lens and adapted to extend generally radially outward therefrom toward an outer surface of one of the chambers of the eye.

5. The apparatus of claim 4 wherein the haptic is configured for mounting in the posterior chamber of the eye.

6. The apparatus of claim 4 wherein the first lens has convex and concave refracting surfaces and wherein the second lens has two convex refracting surfaces and wherein one of the convex refractive surfaces of the second lens is precisely fitted with the concave refracting surface of the first lens and wherein the haptic extends generally radially outward from a peripheral area of the first lens.

7. The apparatus of claim 4 wherein the first lens, second lens and haptic are configured for mounting the first lens in a corneal direction and the second lens in a retinal direction within an eye.

8. The apparatus of claim 4 wherein the intraocular achromatic lens is configured for positioning the first lens in a retinal direction and the second lens in a corneal direction.

9. The apparatus of claim 4 wherein the first lens has convex and concave refracting surfaces and wherein the second lens has convex and planar refracting surfaces and wherein the convex refracting surface of the second lens is precisely fitted with the concave refracting surface of the first lens.

10. The apparatus of claim 4 wherein the first lens has convex and concave refracting surfaces and wherein the second lens has convex and concave refracting surfaces and wherein the concave refracting surface of the first lens and the convex refracting surface of the second lens are precisely interfitted and are joined at the interface.

11. The apparatus of claim 4 wherein the first lens has concave and planar refracting surfaces and wherein the second lens has planar and concave refracting surfaces and wherein the lenses are joined at the planar surfaces with the interface.

12. The apparatus of claim 4 wherein the first lens comprises convex and planar refracting surfaces and wherein the second lens comprises planar and concave refracting surfaces and wherein the first and second lenses are joined at the planar refracting surfaces.

13. An intraocular lens apparatus comprising an achromatic lens in the form of an intracorneal lamellal implant or adapted for aqueous iris fixation or adapted to be fixated within the vitreous, and capable of use in combination with other lenses, either internal or external, or adapted to be placed in an orientation to produce prismatic effects.

14. An intraocular lens apparatus comprising an achromatic intraocular lens adapted for mounting within a eye to enhance color correction and image quality.

15. An intraocular lens apparatus comprising an achromatic lens comprising plural refracting lens element layers of similar materials having different indices of refraction combined together in optical alignment and adapted to be mounted within a human eye.

16. The achromatic lens of claim 15 further comprising a haptic extending from the lens for mounting the lens within a human eye.

17. An intraocular achromatic lens system comprising two intraocular lenses having distinct refractive indices and distinct optical powers for surgically positioning in optical alignment within an eye, the plural lenses being joined together as an achromatic lens and means connected to the achromatic lens for mounting the lens totally within a posterior or anterior chamber of the eye, wherein the achromatic lens is adapted to be mounted within the posterior chamber of the eye.

18. An intraocular achromatic lens comprising a first lens having a first refractive index and a second lens having a second refractive index, the first lens and the second lens being joined together at an interface to form an achromatic lens, the achromatic lens having a size suitable for positioning in an anterior or a posterior chamber of an eye and the achromatic lens having a peripheral mounting element for mounting the achromatic lens within one of the posterior or anterior chambers of the eye, wherein the mounting means comprises a haptic connected to a peripheral portion of one of the lenses which make up the achromatic lens and adapted for extending generally radially outward therefrom toward an outer surface of one of the chambers of the eye.

19. The apparatus of claim 18, wherein the haptic is configured for mounting in the posterior chamber of the eye.

20. The apparatus of claim 18, wherein the first lens has convex and concave refracting surfaces and wherein the second lens has two convex refracting surfaces and wherein one of the convex refractive surfaces of the second lens is precisely fitted with the concave refracting surface of the first lens and wherein the haptic extends generally radially outward from a peripheral area of the first lens.

21. The apparatus of claim 18, wherein the first lens, second lens and haptic are configured for mounting the first lens in a corneal direction and the second lens in a retinal direction within an eye.

22. The apparatus of claim 18, wherein the intraocular achromatic lens is configured for positioning the first lens in a retinal direction and the second lens in a corneal direction.

23. The apparatus of claim 18, wherein the first lens has convex and concave refracting surfaces and wherein the second lens has convex and planar refracting surfaces and wherein the convex refracting surface of the second lens is precisely fitted with the concave refracting surface of the first lens.

24. The apparatus of claim 18, wherein the first lens has convex and concave refracting surfaces and wherein the second lens has convex and concave refracting surfaces and wherein the concave refracting surface of the first lens and the convex refracting surface of the second lens are precisely interfitted and are joined at the interface.

25. The apparatus of claim 18, wherein the first lens has concave and planar refracting surfaces and wherein the second lens has planar and concave refracting surfaces and wherein the lenses are joined at the planar surfaces with the interface.

26. The apparatus of claim 18, wherein the first lens comprises convex and planar refracting surfaces and wherein the second lens comprises planar and concave refracting surfaces and wherein the first and second lenses are joined at the planar refracting surfaces.

27. An achromatic lens comprising plural refracting lens element layers of similar materials having different indices of refraction combined together in optical alignment to form an achromatic lens, further comprising a haptic extending from the lens for mounting the lens within a human eye.

* * * * *

UNITED STATES PATENT AND TRADEMARK OFFICE
CERTIFICATE OF CORRECTION

PATENT NO. : 5,201,762

DATED : April 13, 1993

INVENTOR(S) : Frederick A. Hauber

It is certified that error appears in the above-identified patent and that said Letters Patent is hereby corrected as shown below:

On the title page, under item [54] and column 1, line 2, "ARCHROMATIC" should be --ACHROMATIC--.

Signed and Sealed this

Twenty-third Day of November, 1993

Attest:

BRUCE LEHMAN

Attesting Officer          Commissioner of Patents and Trademarks